(12) United States Patent
Westlund et al.

(10) Patent No.: US 6,643,550 B2
(45) Date of Patent: Nov. 4, 2003

(54) MULTI-POLAR CONNECTOR

(75) Inventors: Randy Westlund, Minneapolis, MN (US); Gwen Crevensten, Minneapolis, MN (US); Christopher M. Zerby, New Brighton, MN (US); Paul E. Zarembo, Vadnais Heights, MN (US); Brian D. Soltis, St. Paul, MN (US); Gregory R. Ley, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 315 days.

(21) Appl. No.: 09/738,401

(22) Filed: Dec. 15, 2000

(65) Prior Publication Data

US 2003/0036779 A1 Feb. 20, 2003

(51) Int. Cl.[7] .................................................. A61N 1/18
(52) U.S. Cl. ........................... 607/37; 607/38; 607/116; 607/122; 607/132; 439/527; 439/592; 439/668; 439/874
(58) Field of Search ............................. 607/37–38, 116, 607/119, 122–123, 126, 132; 439/527, 585, 592, 668–669, 736, 874–5, 877, 908–9

(56) References Cited

U.S. PATENT DOCUMENTS

| | | | |
|---|---|---|---|
| 4,469,104 A | 9/1984 | Peers-Trevarton | 128/419 |
| 4,572,605 A * | 2/1986 | Hess | 439/585 |
| 4,922,607 A * | 5/1990 | Doan et al. | 29/879 |
| 4,934,367 A | 6/1990 | Daglow et al. | 439/527 |
| 4,971,057 A | 11/1990 | Theres | 128/419 |
| 5,012,807 A | 5/1991 | Stutz, Jr. | 128/419 |
| 5,070,605 A | 12/1991 | Daglow et al. | 29/842 |
| 5,076,270 A | 12/1991 | Stutz, Jr. | 128/419 |
| 5,231,996 A | 8/1993 | Bardy et al. | 128/785 |
| 5,267,564 A | 12/1993 | Barcel et al. | 128/634 |
| 5,304,219 A | 4/1994 | Chernoff et al. | 607/122 |
| 5,843,141 A | 12/1998 | Bischoff et al. | 607/37 |
| 6,208,900 B1 | 3/2001 | Ecker et al. | 607/17 |

* cited by examiner

Primary Examiner—Henry Bennett
Assistant Examiner—Shawntina Fuqua
(74) Attorney, Agent, or Firm—Schwegman, Lundberg, Woessner & Kluth, P.A.

(57) ABSTRACT

A connector for connecting to an energy source such as a pulse generator for a cardiac stimulator system. The connector assembly includes a pin, at least one ring and a sleeve composed of an insulative hard polymer molded between the pin and ring such that the sleeve provides electrical insulation between the pin and ring and mechanically couples the pin and ring.

34 Claims, 18 Drawing Sheets

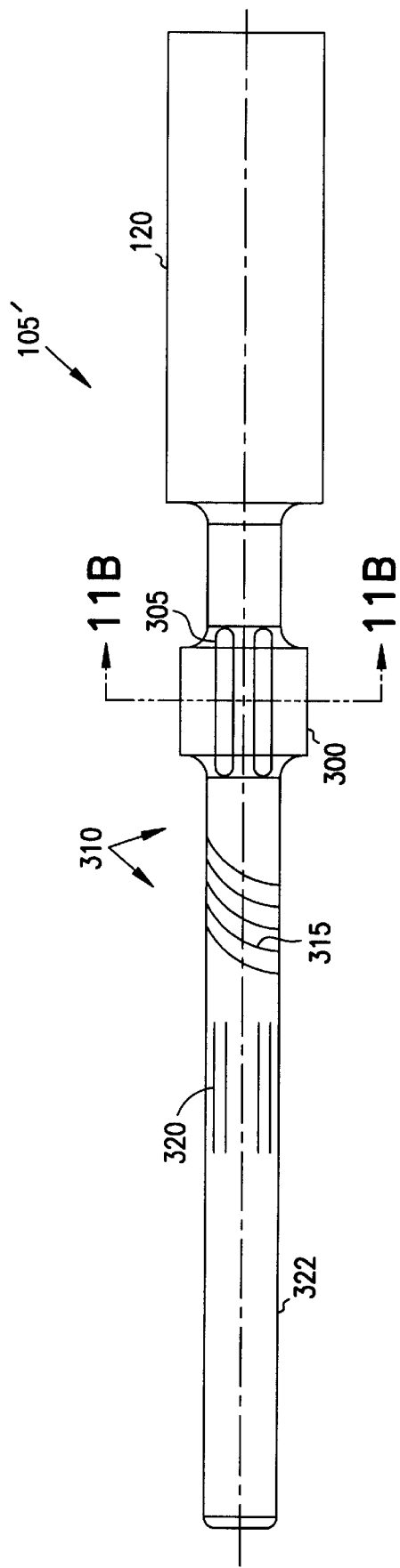
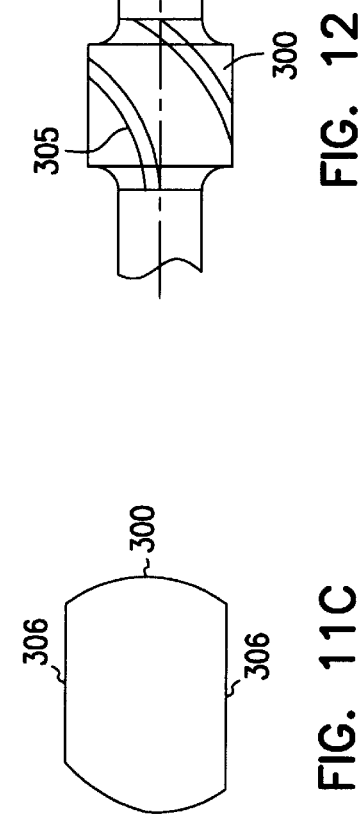
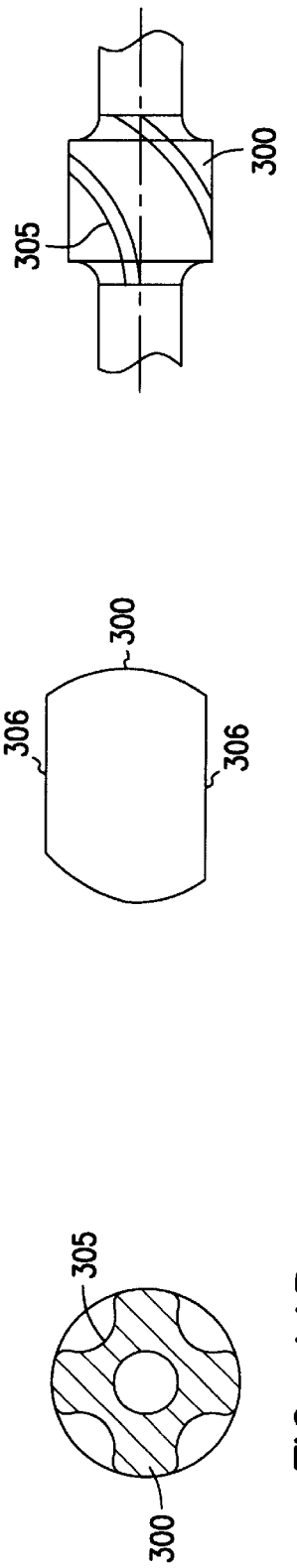
FIG. 11A
FIG. 11B
FIG. 11C
FIG. 12

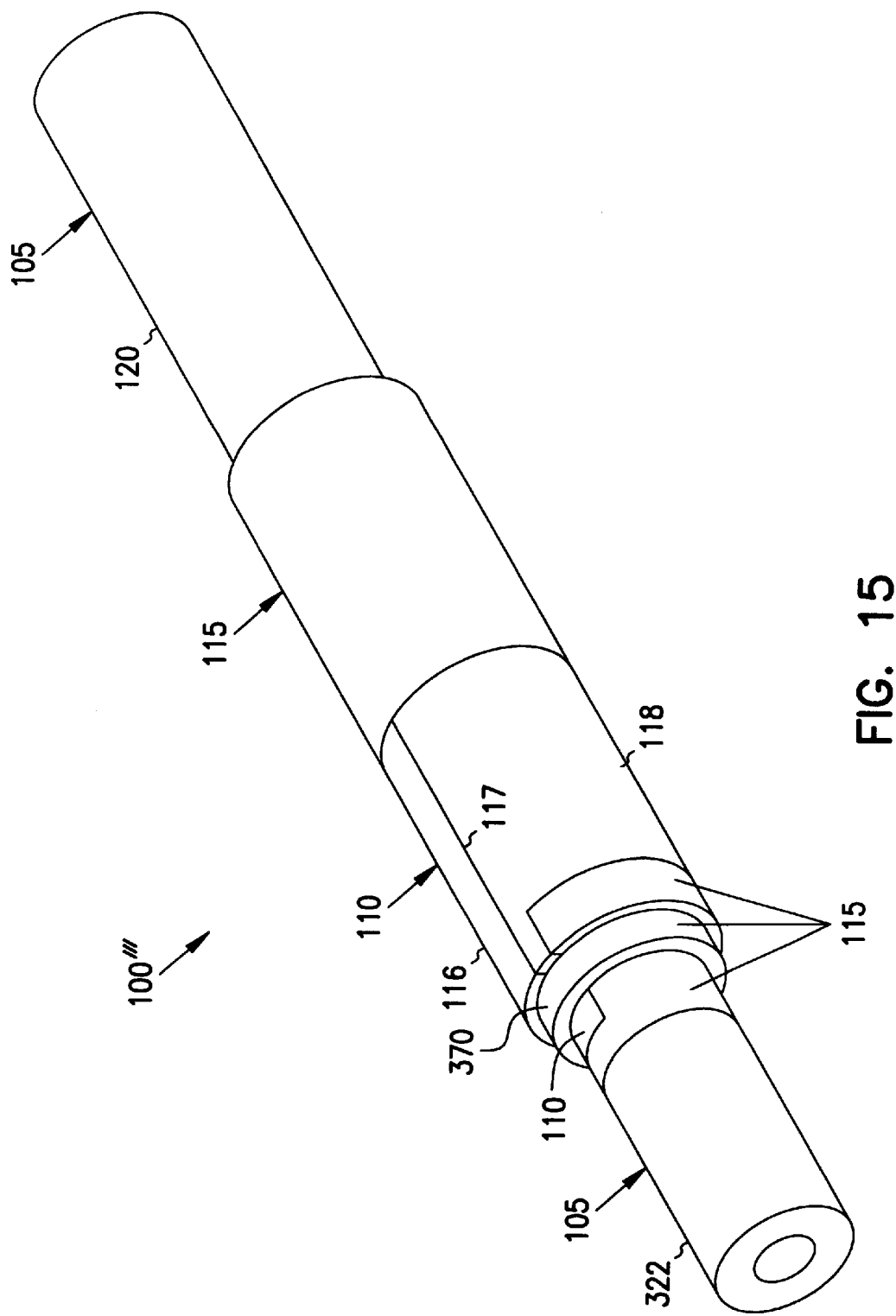

MULTI-POLAR CONNECTOR

TECHNICAL FIELD

This application relates to a connector for connecting a lead to an energy source such as a cardiac stimulator.

BACKGROUND

Connector assemblies are used to couple a conductor with a device. For instance, a connector is used to couple a cardiac stimulator system such as a pacemaker, an anti-tachycardia device, a cardioverter or a defibrillator with a lead having an electrode for making contact with a portion of the heart.

When leads with multiple conductors are involved, the conductors are individually, mechanically and electrically coupled with the pulse generator at a proximal end of the multiple conductors. The multiple conductors at the proximal end are electrically insulated from each other to prevent shorts and limit electrical leakage between conductors. Medical adhesive is used to bond and insulate the multiple conductors at the proximal end of the lead. However, the process of using medical adhesive is timely and costly. In addition, the medical adhesive bonds inconsistently, sometimes resulting in mechanical and electrical separation between the components, and resulting in dimensional inconsistency.

The proximal end of the lead includes a terminal connection which provides the electrical and mechanical connection between the pacemaker and the proximal end of the lead. When inserted into the pacemaker, the components of the terminal connection undergoes axial stress as the implanter forces the proximal end of the lead into the pacemaker. After inserted, the implanter may pull on the lead to ensure the terminal end is sufficiently seated in the pacemaker, placing additional axial stress on the terminal connection.

In addition, connector assemblies are subjected to a variety of tests including axial loading to test the strength of the coupling of the components. Existing connector assemblies often include numerous components and require numerous steps in the assembly process to provide the desired connection between the components. Connector designs include components that are welded together, bonded with adhesive or a combination of both. Welded components require subassembly prior to assembly with other components and may require additional components suitable for making weld connections. Bonding components with adhesive also requires subassembly. Additionally, bonding components with adhesive requires time to cure and is a messy process. Connector designs including components that are welded together or bonded with adhesive or a combination of both add additional elements and steps to the manufacturing and assembly process. These additional elements increase the complexity of the component and can represent a bottle-neck in the manufacturing and assembly process of the connector assembly.

SUMMARY

A connector assembly includes a pin extending from a pin distal end to a pin proximal end. The pin further includes an intermediate portion between the distal end and the proximal end. In addition, the connector assembly includes at least one ring extending from a ring distal end to a ring proximal end and having a ring intermediate portion therebetween. A molded insulative polymer is between the pin and the ring, the polymer mechanically couples the pin and the ring, and the insulative polymer insulates the pin from the ring.

Several options for the connector assembly are as follows. For instance, in one option, the pin has a first outer diameter and the ring has a second outer diameter, and the first diameter is substantially the same as the second diameter. In another option, the connector assembly further includes a second ring, and the insulative polymer is between the pin, the first ring and the second ring, and the second ring is mechanically coupled to the pin by the polymer. In another example, the ring further includes at least one passage, and the molded polymer is molded within the at least one passage. The pin includes, in another option, at least one chamfer, and the molded insulative polymer is molded within the chamfer.

Other options are follows. For instance, the pin optionally has at least one chamfer formed thereon. In another option, the ring includes a full boss and a full chamfer, and/or the ring includes an extension thereon, the extension having a partial boss and a partial chamfer thereon. In yet another option, an interior surface of the ring includes grooves formed thereon, or the grooves are oblique to a longitudinal axis of the ring. The pin further optionally includes a boss formed thereon, and/or the pin boss further includes grooves formed thereon, and/or the pin further includes grooves formed on a distal portion of the pin.

In another embodiment, an assembly comprises a connector assembly. The connector assembly includes a pin extending from a pin distal end to a pin proximal end, and having a pin intermediate portion therebetween. The connector assembly further includes at least one ring extending from a ring distal end to a ring proximal end and having a ring intermediate portion therebetween, and a molded insulative polymer between the pin and the ring, the polymer mechanically couples the pin and the ring, and the insulative polymer insulates the pin from the ring. The assembly further includes a lead having a lead body, the lead coupled with the connector assembly.

Several options for the assembly are as follows. For instance, the connector assembly has a first outer diameter, the lead having a second outer diameter, and the first outer diameter and the second outer diameter are substantially the same. In another option, the connector assembly further includes a groove on an outer diameter of the connector assembly, the groove configured to receive a portion of a pulse generator, and/or the connector assembly further includes a second groove on the outer diameter. In another option, a second ring, and a third ring, and the insulative polymer is between the pin, the first ring, the second ring, and the third ring, the second ring and the third ring mechanically coupled to the pin by the polymer. In yet another option, the pin further includes a pin boss formed thereon, and the pin boss further includes grooves formed thereon.

In one embodiment, a method comprises forming a pin, forming at least one ring, molding a sleeve between the pin and the ring, including mechanically coupling the pin with the ring. Several options for the method are as follows. For instance, the method further comprises coupling a lead with the pin, the at least one ring, and the sleeve to form an assembly having an isodiametric outer diameter. In another option, the method further includes forming a second ring, and molding the sleeve between the ring, the pin, and the second ring. In yet another option, the method further includes swaging a conductor within a passage of the at least one ring, and/or welding a conductor within a passage of the at least one ring. A further option for the method includes forming an extension on the ring, and/or forming a partial boss and a partial chamfer on the extension.

The construction of the connector does not require weld joints or adhesive bonds between components. The result is a connector with fewer components, fewer steps in the assembly process, reduced size and smaller diameter, improved insulative properties and improved mechanical strength. The connector is useful for unipolar, multipolar, uniradial, and co-radial construction.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF DRAWINGS

FIG. 11A is a side elevational view of a pin of a connector assembly as constructed in accordance with one embodiment;

FIG. 11B is a cross-sectional view taken along 11B—11B of FIG. 11A;

FIG. 11C is a cross-section view of a pin of a connector assembly as constructed in accordance with one embodiment;

FIG. 12 is a side elevational view of a portion of a pin of a connector assembly as constructed in accordance with another embodiment;

FIG. 15 is a perspective view of a connector assembly as constructed in accordance with another embodiment;

DETAILED DESCRIPTION OF EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
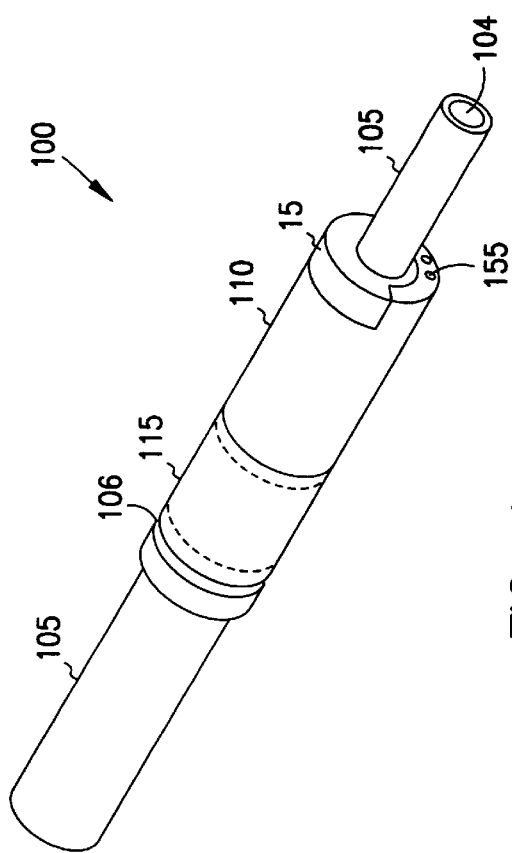
FIG. 1 is a perspective view illustrating a connector assembly as constructed in accordance with one embodiment.
Figure 2:
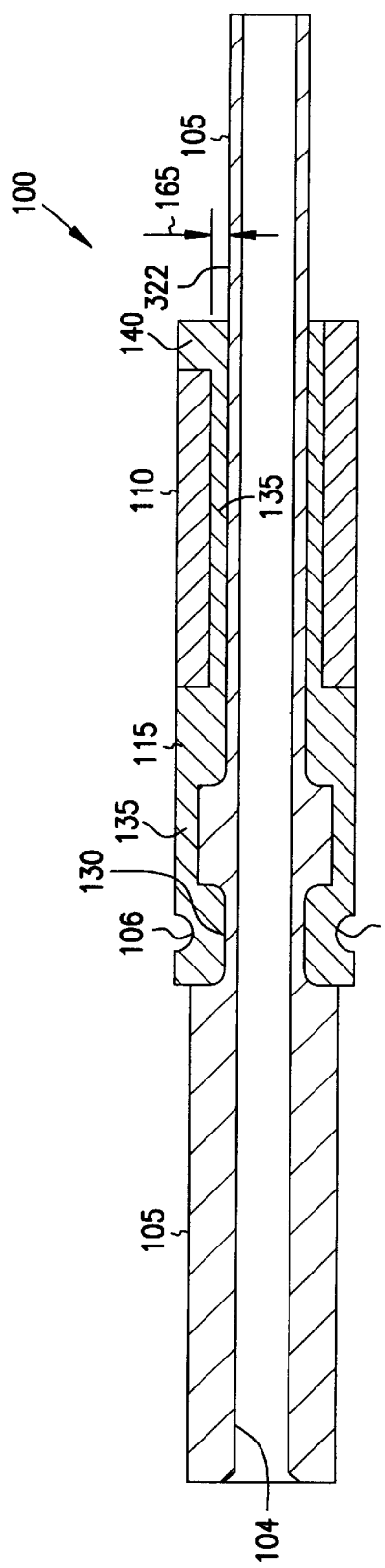
FIG. 2 is a cross-sectional view illustrating a connector assembly as constructed in accordance with one embodiment.

FIGS. 1 and 2 illustrate a connector assembly 100 which connects a conductor to a device or an energy source. The connector assembly 100 includes a pin 105, at least one ring 110 and a unitary sleeve 115 formed from a molded insulative hard polymer. In one option, the pin 105 includes a lumen 104 therethrough, which is sized and configured to receive a stylet or guidewire therethrough. Alternatively, the lumen 104 is configured to receive other types of devices therethrough. In yet another option, the pin 105 is solid, for example the lumen 104 is filled with the hard polymer.

Various materials are suitable for the insulative hard polymer. For example, suitable materials include, but are not limited to, PEEK (TM), polyurethane, tecothane, acrylic, polycarbonate, polysulfone, high durometer silicone, materials having a durometer of about 80 Shore a, or materials having a dielectric constant of 300–500V/0.001 inches.

The insulator polymer separates the pin 105 and the ring 110. The insulative hard polymer of the sleeve 115 provides improved electrical isolation between the pin 105 and ring 110 and also provides improved mechanical coupling between the pin 105 and ring 110. Although the connector assembly 100 shown in FIG. 1 illustrates a bipolar connector, the molded sleeve 115 is suitable for use with a unipolar or multipolar design.

Figure 5:
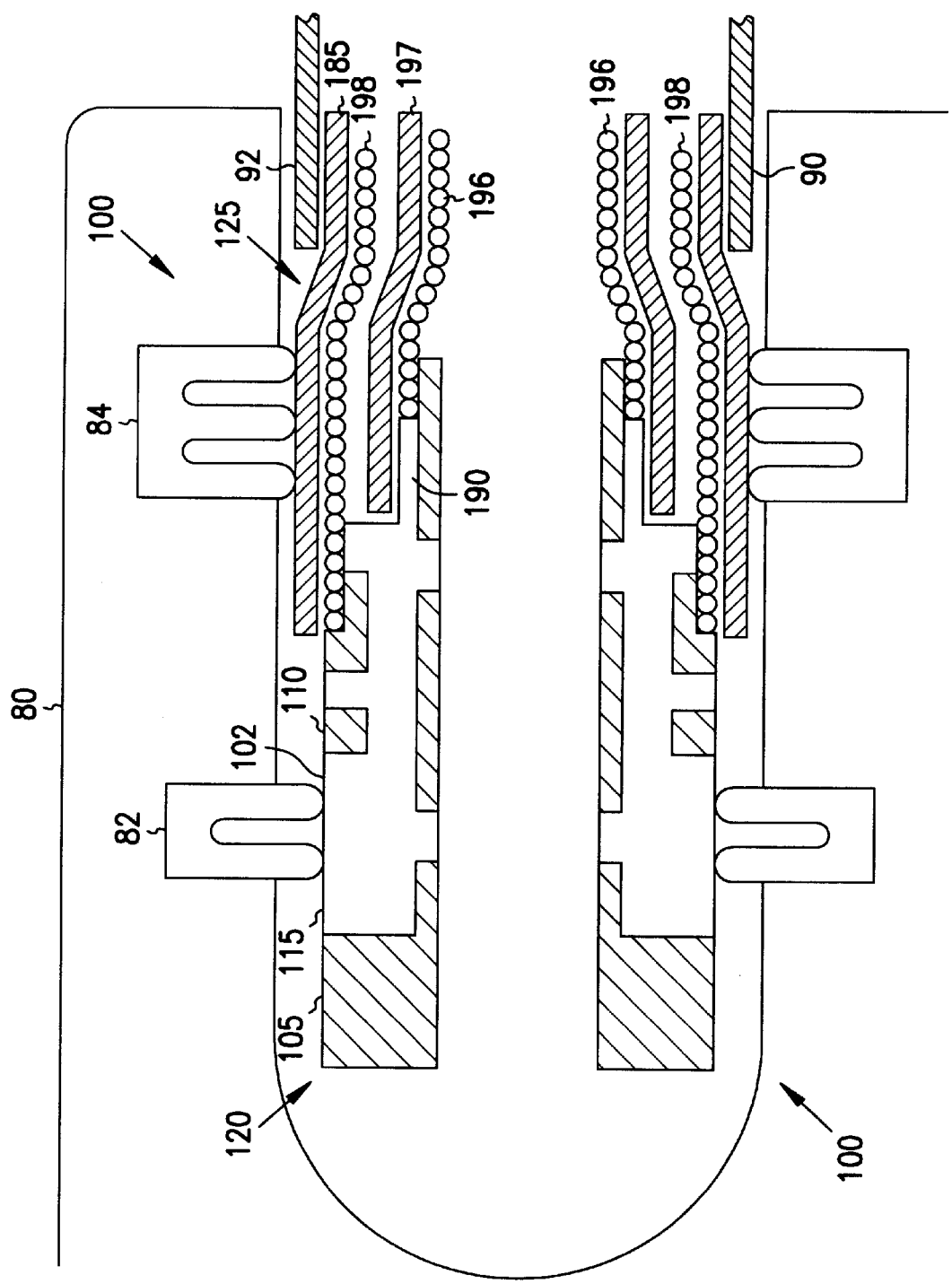
FIG. 5 is a cross sectional view illustrating a portion of a connector assembly as constructed in accordance with one embodiment.
Figure 6:
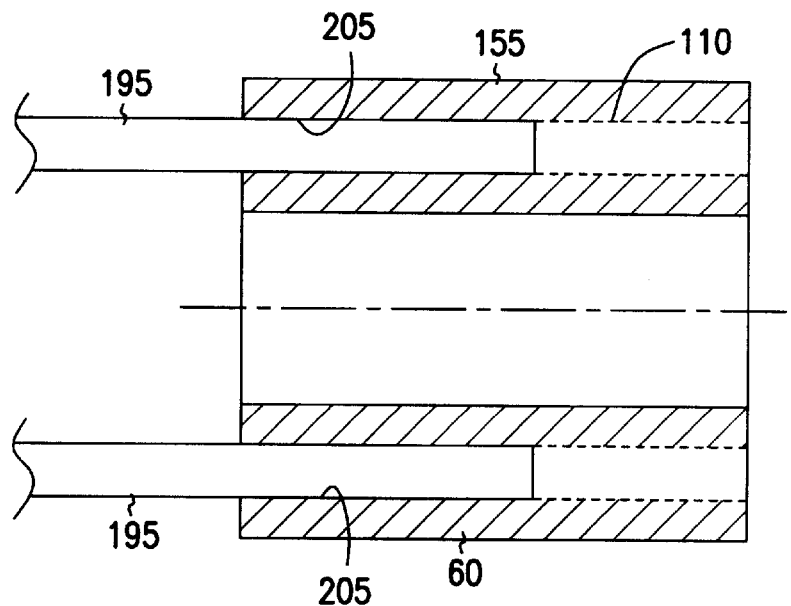
FIG. 6 is a cross-sectional view of a portion of a ring as constructed in accordance with one embodiment.

The sleeve 115 is received within a portion of an energy source such that the interface between the connector assembly 100 and portion of the energy source prevents body fluid from entering the energy source. In one embodiment, the sleeve 115 includes a groove 106 for mating with a portion, such as a projection, of the pulse generator 80 (FIG. 5). In another option, the sleeve 115 includes a ridge for mating with a portion of the pulse generator 80 (FIG. 5). The groove 106 allows for the physician to receive a tactile indication of when a connector assembly 100 has been properly inserted into the pulse generator 80 (FIG. 5).

FIG. 2 shows one embodiment, the distance 165 between a portion of the pin 105 and a portion of the ring 110 is in the range of about 0.005 inches which is achieved by use of the molded polymer for the sleeve 115. One benefit of forming the sleeve 115 from the insulative hard polymer is that it allows the pin 105 and ring 110 to be assembled in closer proximity while providing the required insulative properties between the pin 105 and ring 110. Thus, for a given electrical performance, the molded sleeve 115 provides for a connector assembly 100 having smaller dimensions.

FIG. 2 illustrates one example of how the dimensional consistency and mechanical lock is maintained in the longitudinal direction at least in part by a portion of the insulative hard polymer that is molded into at least one chamfer portion 130 of the pin 105. In another option, a proximal portion 135 of the insulative hard polymer is molded proximal to the ring 110, between the pin 105 and ring 110. In a further option, a distal portion 140 of the insulative hard polymer is molded distal to the ring 110.

Figure 3:
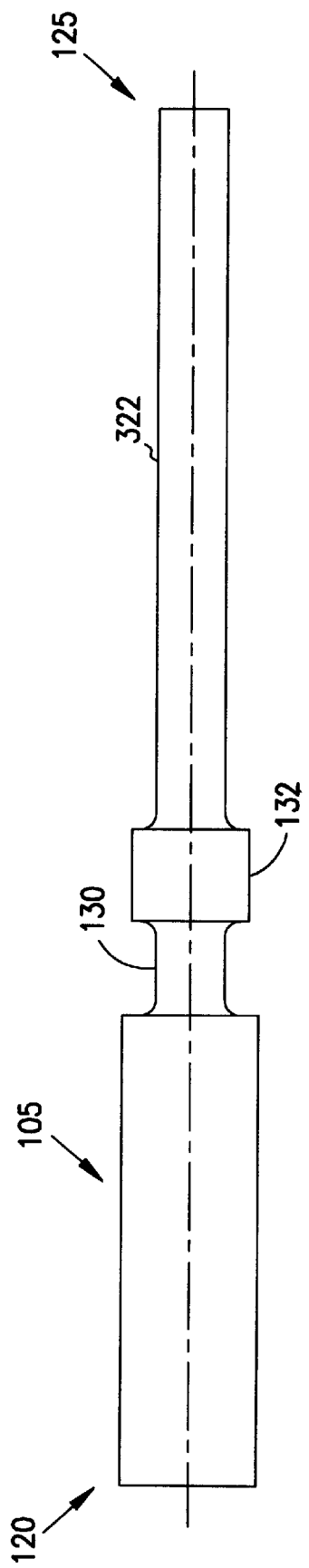
FIG. 3 is a side elevational view illustrating a pin as constructed in accordance with one embodiment.
Figure 4C:
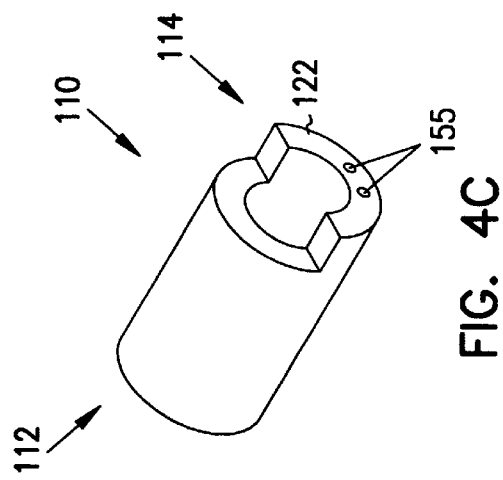
FIG. 4C is a perspective view illustrating a ring as constructed in accordance with one embodiment.
Figure 4D:
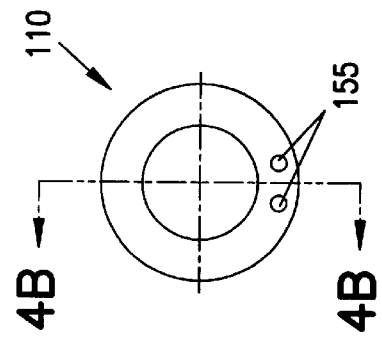
FIG. 4D is an end view illustrating a ring as constructed in accordance with one embodiment.
Figure 4B:
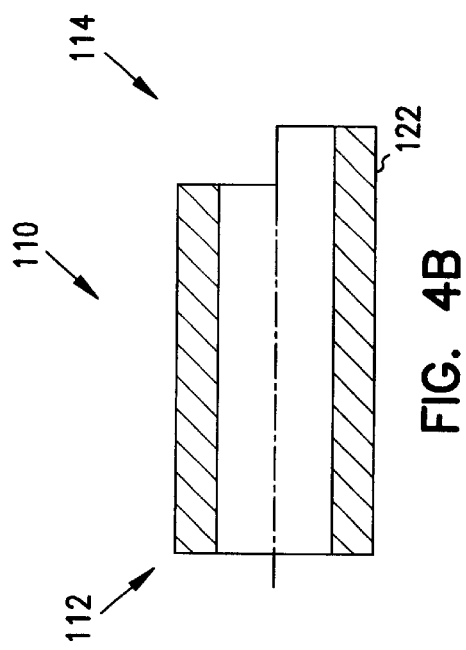
FIG. 4B is a cross-sectional view illustrating a ring as constructed in accordance with one embodiment.
Figure 4A:
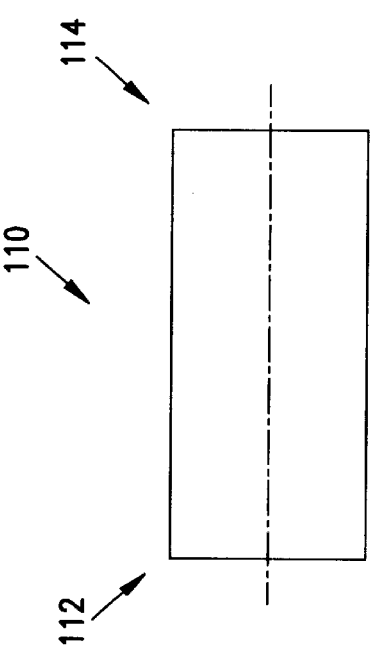
FIG. 4A is a side elevational view illustrating a ring as constructed in accordance with one embodiment.

FIG. 3 illustrates one embodiment of the pin 105 in greater detail, where the pin 105 extends from a proximal end 120 to a distal end 125. The pin 105 includes a chamfer 130 in between the proximal end 120 and the distal end 125. The chamfer 130 receives a portion of the sleeve 115 (FIG. 2) therein, for example, the sleeve 115 (FIG. 2) is molded into the chamfer 130. In another option, the pin 105 includes a boss 132 which is received by the sleeve 115 (FIG. 2). The chamfer 130 and the boss 132, in combination of the sleeve 115 (FIG. 2), assist in preventing axial movement of the sleeve 115 (FIG. 2) relative to the pin 105.

Figure 7:
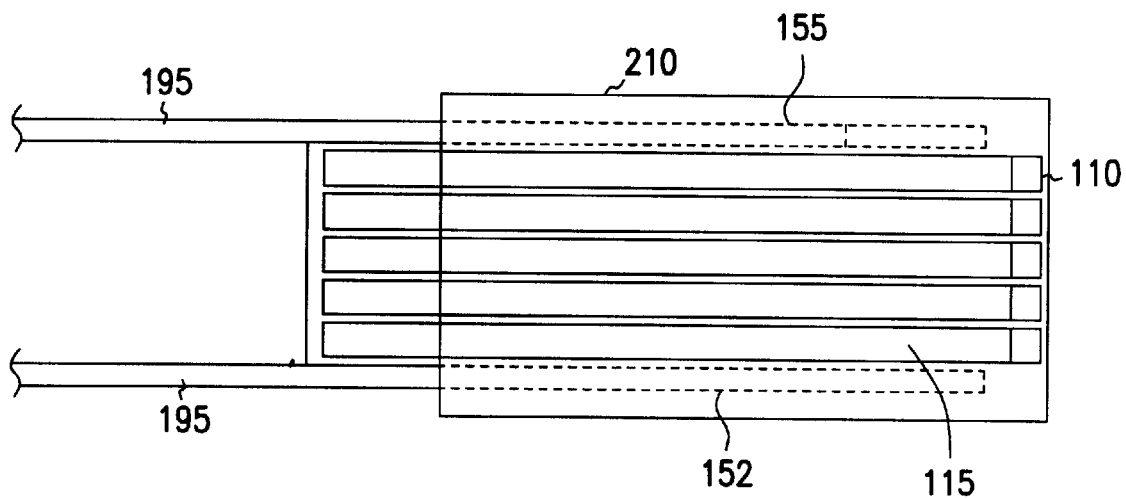
FIG. 7 is a cross-sectional view of a portion of a ring as constructed in accordance with one embodiment.

FIGS. 4A–4D, 6 and 7 illustrate a ring 110 in greater detail. The ring 110 extends from a proximal end 112 to a distal end 114. Disposed at the distal end 114, in one option, is an extension 122. In one option, the extension 122 includes one or more passages 155, which are configured to receive a conductive element therethrough. The passages 155, also shown in FIG. 6, receive the conductive element therethrough. In one embodiment, the conductive elements 195 are secured inside the passages 155 by swaging the ring 110. FIG. 7 illustrates another option in which the ring 110 includes longitudinal grooves 205 on an outer surface 210 of the ring 110. The grooves 205 receive a pair of conductive elements 195 therein. In one option, the conductive elements 195 are welded within the grooves 205. In another option, the conductive elements 195 are crimped within the longitudinal grooves 205.

FIG. 5 illustrates the connector assembly 100 coupled with a lead 90 and disposed within a pulse generator 80. It should be noted that the connector assembly 100 includes, but is not limited to, any of the above or below discussed connector assemblies. The lead 90 includes a lead body 92 having an inner conductor 196, an inner insulative sleeve 197, and an outer coiled conductor 198. The inner coiled conductor 196, in one option, is comprised of two inner conductor elements, each individually insulated and coupled to the pin 105. The outer coiled conductor 198, in one option, is comprised of two inner conductor elements, each individually insulated and coupled to the pin 105.

As mentioned above, the connector assembly 100 is connected to a lead 90 having a first conductive element electrically insulated from a second conductive element. In one embodiment, the first conductive element extends over a portion of the pin 105 and is electrically coupled to the pin 105. In another embodiment, the second conductive element extends over a portion of the ring 110 and electrically coupled to the ring 110. The first conductive element, in one option, is nested within a second conductive element, the first and second conductive elements being coiled in a co-axial manner. In another option, the first conductive element and the second conductive element are wound co-radially. The first conductive element is mechanically and electrically coupled to the pin 105 and the second conductive element is mechanically and electrically coupled to the ring 110. Suitable methods for mechanically and electrically coupling include, but are not limited to, swaging, crimping, and welding.

The sleeve 115 includes an interface portion 190 which receives an inner insulative sleeve 197. The interface portion 190 further abuts the inner coiled conductor 196. The inner insulative sleeve 197 surrounds the inner coiled conductor 196, and isolates the inner coiled conductor 196 from the outer coiled conductor 198. An outer insulative sleeve 185 surrounds the outer coiled conductor 198. The lead body 92 is mounted over the outer insulative sleeve 185.

The connector assembly 100 includes a sealing area 102, which abuts up against a first seal 82 of the pulse generator 80. The first seal 82 comprises a pin seal zone and assists in preventing bodily fluids from entering an implanted pulse generator 80. The connector assembly 100 is further coupled with a lead 90, as discussed above. The pulse generator 80 further includes a second seal 84, which seals to the lead 90. The second seal 84 seals in a ring seal zone.

Figure 8:
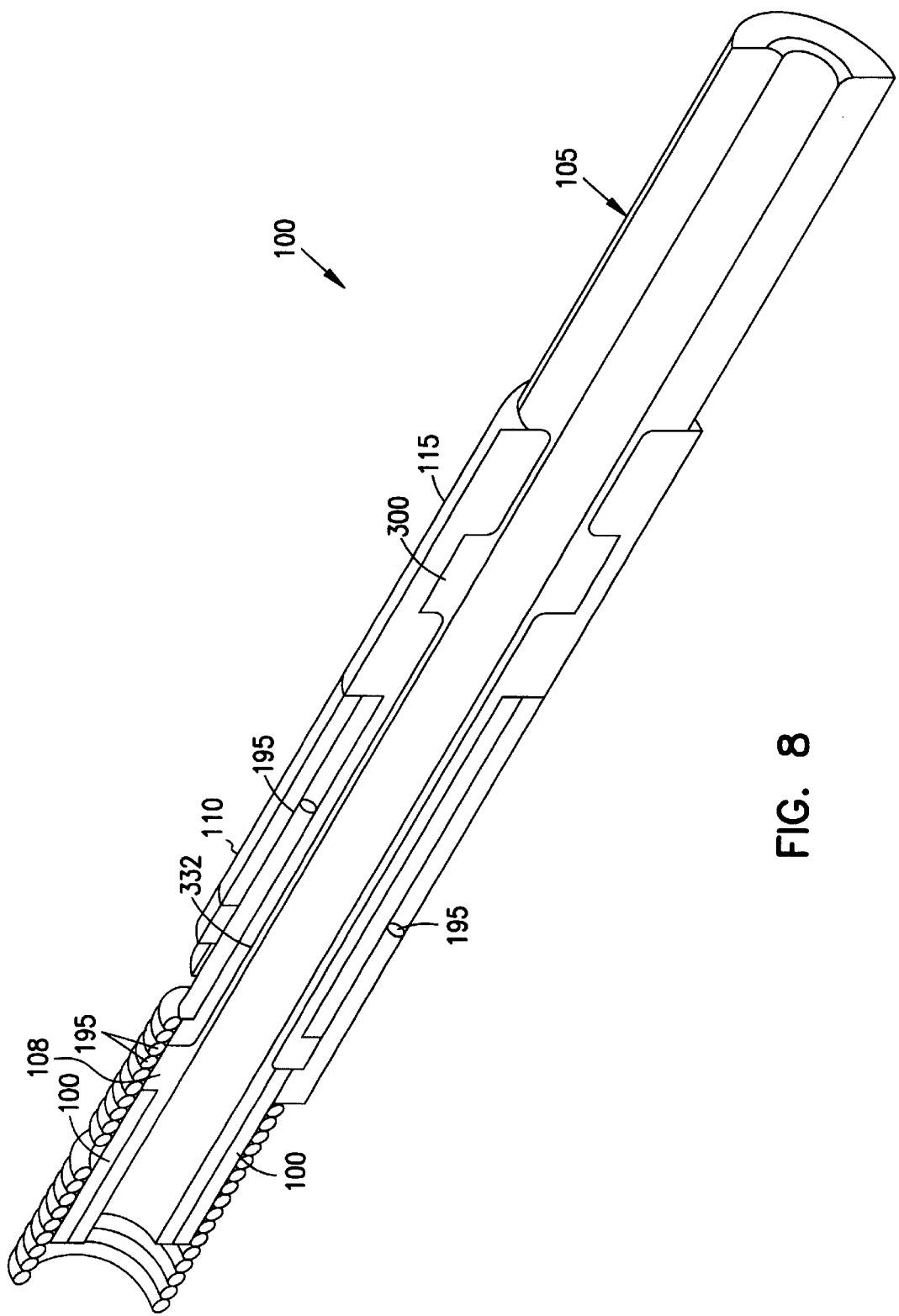
FIG. 8 is a cross-section view of a connector assembly as constructed in accordance with another embodiment.

FIG. 8 illustrates another embodiment of a connector assembly 100. The connector assembly includes the pin 105 and the ring 110, as discussed above. The pin 105, in one option, has a distal chamfer 108. The distal chamfer 108 provides a location for making the electrical connection with the conductive element 195, including, but not limited to, by swaging, welding, and/or conductive epoxy.

Figure 9A:
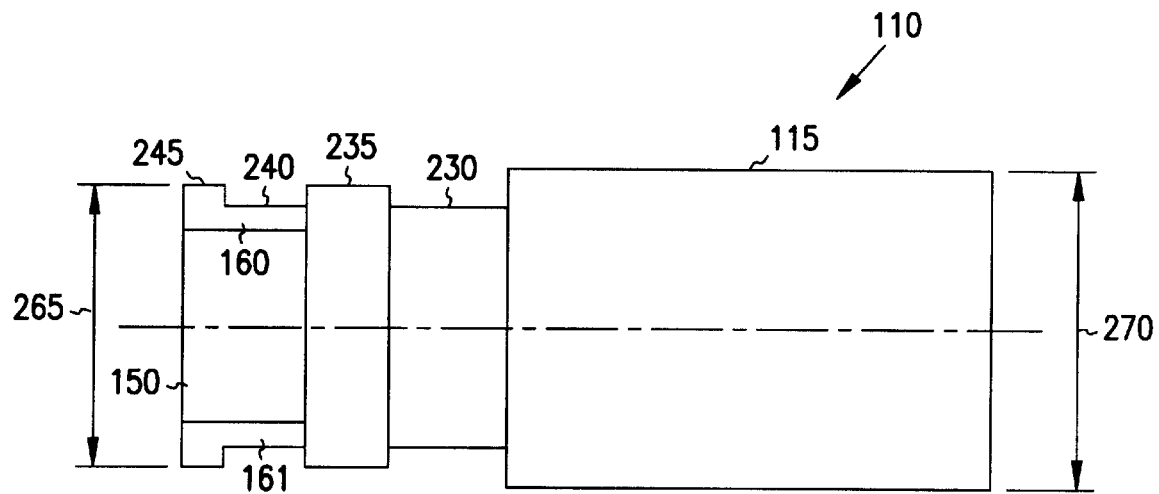
FIG. 9A is a cross-sectional view taken along 9A—9A of FIG. 9D of a ring as constructed in accordance with one embodiment.
Figure 9B:
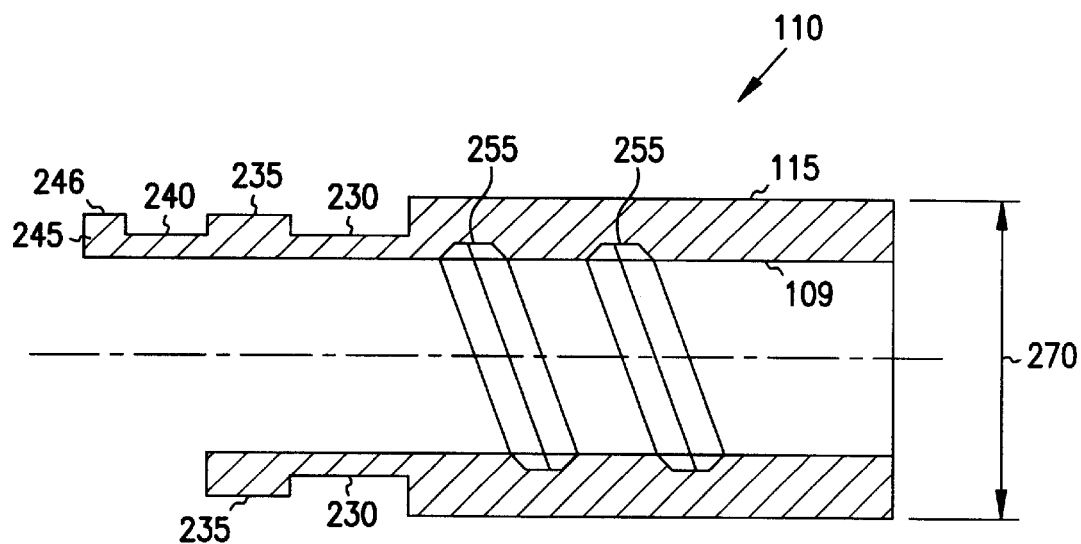
FIG. 9B is a cross-sectional view taken along 9B—9B of FIG. 9D of a ring as constructed in accordance with one embodiment.
Figure 9C:
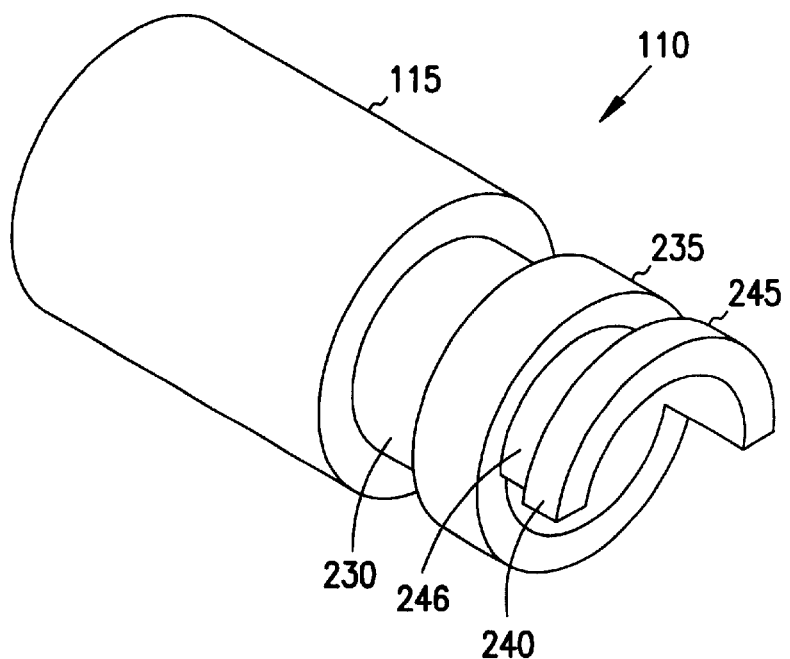
FIG. 9C is a perspective view of a ring as constructed in accordance with one embodiment.
Figure 9D:
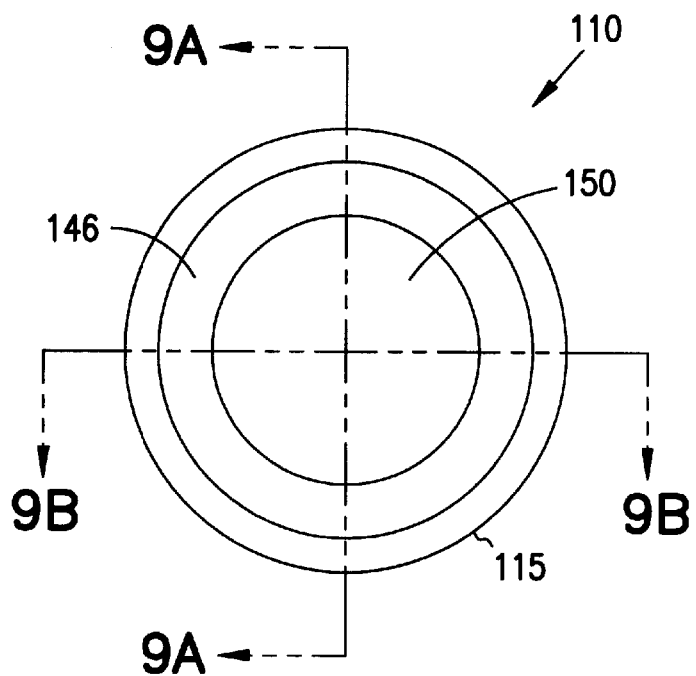
FIG. 9D is an end view of a ring as constructed in accordance with one embodiment.

FIGS. 9A, 9C, 9D illustrate various views of another embodiment of a ring 110. The ring 110 includes a full chamfer 230, a full boss 235, a partial chamfer 240 and a partial boss 245. The full chamfer 230 includes a recess which runs the full and/or substantially the full circumference of the ring 110. The full boss 235 includes a projection which runs the full and/or substantially the full circumference of the ring 110. The partial chamfer 240 and the partial boss 245 make up an extension portion 246 of the ring 110 that runs around at least a portion of the circumference. The extension portion of the unitary ring 110 includes surfaces 160, 161 seen in FIG. 9A. Conductive elements cross over the surfaces 160, 161 and contact the unitary ring 110 in the partial chamfer 240 portion of the ring 110.

FIG. 9B illustrates an embodiment of a ring 110 having grooves 255 on the inner surface 109 of the ring 110 for receiving a portion of the molded unitary sleeve 115. In one embodiment, the grooves 155 are separate angled grooves 155, where the angle is oblique to a longitudinal axis of the ring 110. The grooves may take a different form and other embodiments include but are not limited to, grooves 155 running circumferentially and/or grooves that are continuous and run in a thread-like configuration.

Figure 10A:
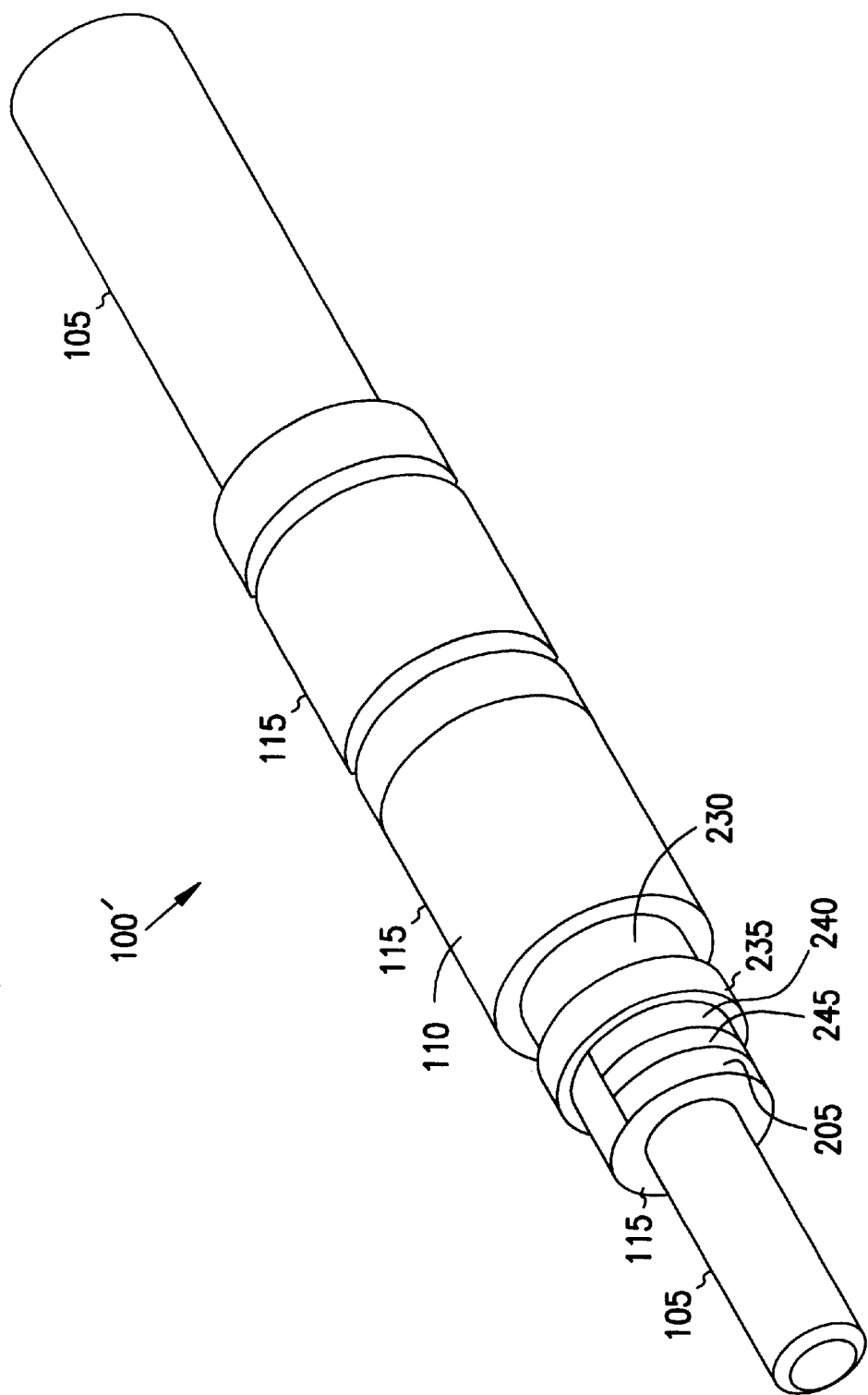
FIG. 10A is a perspective view of a connector assembly as constructed in accordance with another embodiment.
Figure 10B:
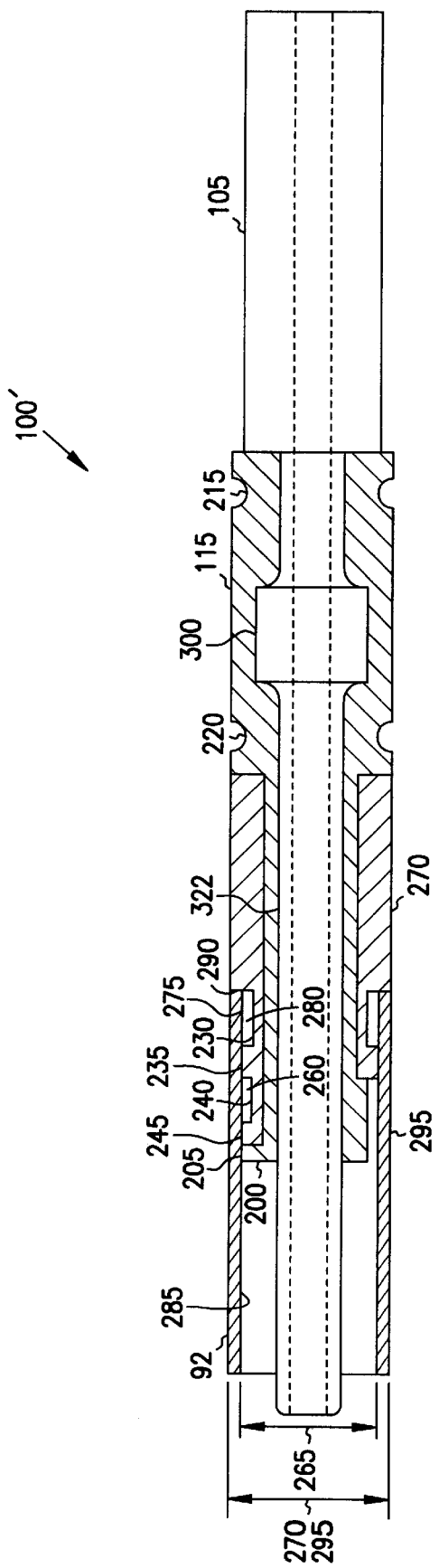
FIG. 10B is a cross-sectional view of a connector assembly as constructed in accordance with one embodiment.

Referring to FIG. 10A, the ring 110 having a full chamfer 230, a full boss 235, a partial chamfer 240 and a partial boss 245, as discussed above, are shown incorporated into a connector assembly 100'. The sleeve 115 further includes, optionally, a partial sleeve boss 206 for allowing passage of a conductor element. FIG. 10B illustrates the ring 110 in which a full boss 235 and a partial boss 245 are adapted for receiving a lead body 92 thereover. The full boss 235 and the partial boss 245 have a reduced outer diameter 265 relative to the outer diameter 270 of the outer surface 210 of the ring 110. The lead body 92 further fits over the partial chamfer 240 and the full chamfer 230 and abuts a distal edge 290 of the ring 110. An area defined by a lead inner surface 285 and the full chamfer 230 defines a bond zone 275 for use in bonding the lead body 92 to the connector assembly 100'. In one option, the full chamfer 230 is adapted for receiving a coupling ring 280 thereon.

Figure 10C:
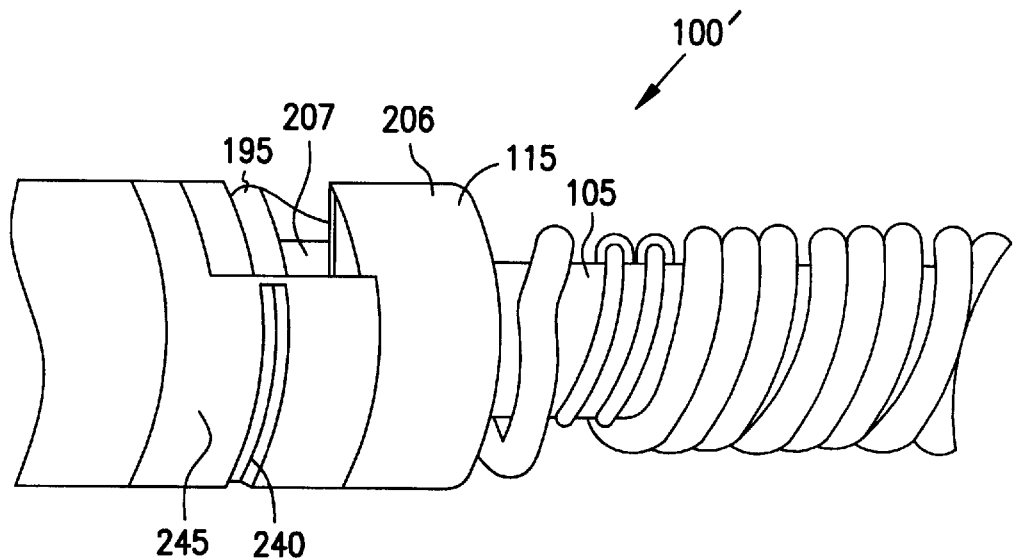
FIG. 10C is a perspective view of a portion of a connector assembly as constructed in accordance with another embodiment.
Figure 10D:
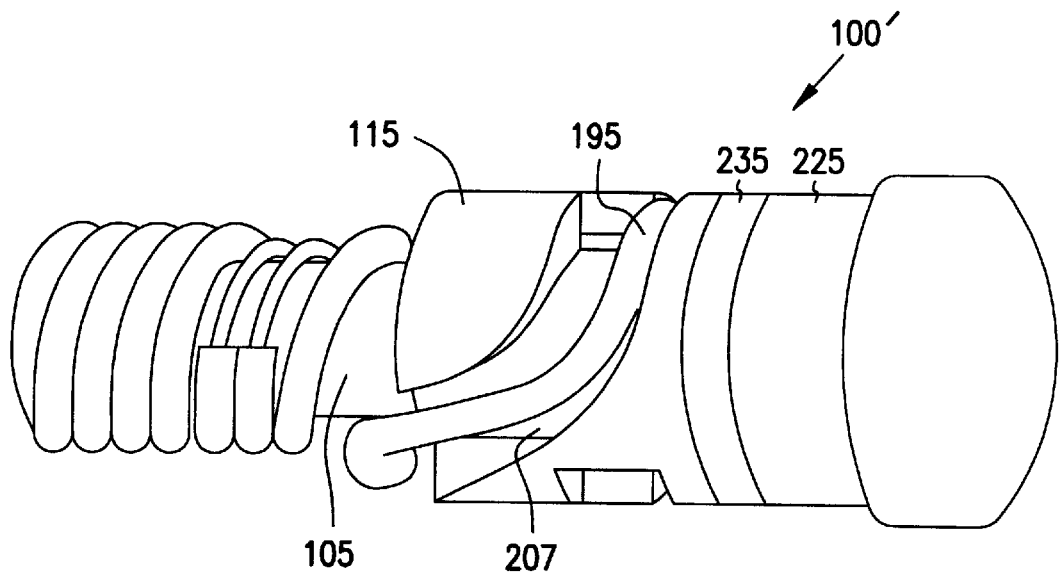
FIG. 10D is a perspective view of a portion of a connector assembly as constructed in accordance with another embodiment.

FIGS. 10C and 10D illustrate another embodiment for the ring 110 and the sleeve 115 of the connector assembly 100'. The ring 110 has a full boss 235, a partial chamfer 240 and a partial boss 245. The sleeve 115 further includes, optionally, a partial sleeve boss 206' and a partial sleeve chamfer 207 for allowing passage of a conductor element 195. The chamfer 207 in one option comprises a spiral channel which isolates the conductor element 195. In a further option, the chamfer 207 is wider than the conductor element 195, allowing for the chamfer 207 to be backfilled, for example, by epoxy or welding material. It should be noted that the conductor element 195 is disposed within the chamfer 195 after the welding of the sleeve 115. However, in another option, the conductor element 195 is disposed within the chamfer 195 before the welding of the sleeve.

Referring to FIGS. 10A, 10B, 10C, and/or 10D, the coupling ring 280 provides a bonding surface for coupling the lead body 92 to the connector assembly 100'. The coupling ring 210 is confined within the full chamfer 230 and is of a material suitable for bonding to the lead body 92. The coupling ring 280 sits within the full chamfer 230 of the ring 110, and the ring 110 provides structural rigidity that helps to confine the coupling ring 210. The coupling ring 280 optionally comprises a molded piece that is molded onto the ring 110. In one embodiment, the coupling ring 280 is molded through openings in the unitary ring 110 that extend to the full chamfer 230. The coupling ring 280 assists in securing the ring 110 relative to the sleeve 115 and pin 105. Other embodiments include but are not limited to a coupling band that opens and snaps into place or expands to fit over the ring 110 and contracts to fit within the full chamfer 230. In one option, the coupling ring 280 is comprised of the same material as the lead body 92, for instance a polymer.

In FIG. 10B, the area defined by the lead inner surface 285 and the partial chamfer 240 defines a conductor coupling zone 260. a conductor element is positioned inside the partial chamfer 240 where it is coupled to the unitary ring 110. In one option, the conductor is welded inside the partial chamfer 240. Suitable welding techniques include, but are not limited to, laser welding, resistance welding or butt welding. Other embodiments for coupling the conductor element inside the partial chamfer 240 include but are not limited to using a conductive adhesive to couple the conductive element or positioning an annular member over the conductor element and swaging the annular member.

The lead body 92 has a lead body outer diameter 295 which coincides with the ring outer diameter 270 forming a continuous uninterrupted profile, and an isodiametric outer profile for the lead body 92 and the ring 110. This also provides a continuous and isodiametric profile for the connector assembly 100' and lead body 92 well suited for implantation applications.

The sleeve 115 optionally includes a first sleeve chamfer 215 and a second sleeve chamfer 220 for mating with a corresponding portion of an implantable device. In one embodiment, the unitary sleeve 115 includes a keyway groove which requires a quarter turn to complete engagement with an implantable device such as a pulse generator header.

FIG. 11A illustrates a pin 105' having a boss 300 including pin boss grooves 305. As illustrated in FIG. 11B, the pin boss grooves 305 create cavities for receiving the unitary sleeve 115 therein. The pin boss grooves 305 help to prevent rotation of the unitary sleeve 115 about the pin 105'. The pin boss grooves 305, in one option, are longitudinal grooves. Other embodiments include, but are not limited to, angled grooves, threaded portions, or grooves having an arcuate shape, such as shown in FIG. 12. FIG. 11C illustrates yet another option for the boss 300 which includes one or more flats 306, and optionally includes the grooves of FIG. 11A, 11B, or 12. The one or more flats 306 assists in providing rotational stability, and provides a less complex manufacturing process than the grooves.

Referring again to FIG. 11A, the pin 105', in another option, has pin ridges 310. The pin ridges 310 include, in one option, one or more longitudinal pin ridges 320 located on the pin 105', for example at a distal portion 322. The longitudinal pin ridges 320 extend outward from the distal portion 322 and create cavities for receiving the sleeve 115. The pin ridges 310 include, in another option, angled pin ridges 315 in addition to or in alternative to the longitudinal pin ridges 320. The angled pin ridges 315, in one option, are formed at an angle which is oblique to the longitudinal axis of the pin 105'. The angled pin ridges 315 extend outward from the distal portion 322 and create cavities for receiving the unitary sleeve 115. Other embodiments for the angled pin ridges 315 include, but are not limited to, thread like ridges. The pin ridges 310 assist in preventing rotation of the unitary sleeve 115 about the pin 105'. Other embodiments include but are not limited to longitudinal or angled grooves in the distal portion 322 of the pin 105' to help prevent rotation of the unitary sleeve 115 about the pin 105'.

Figure 13:
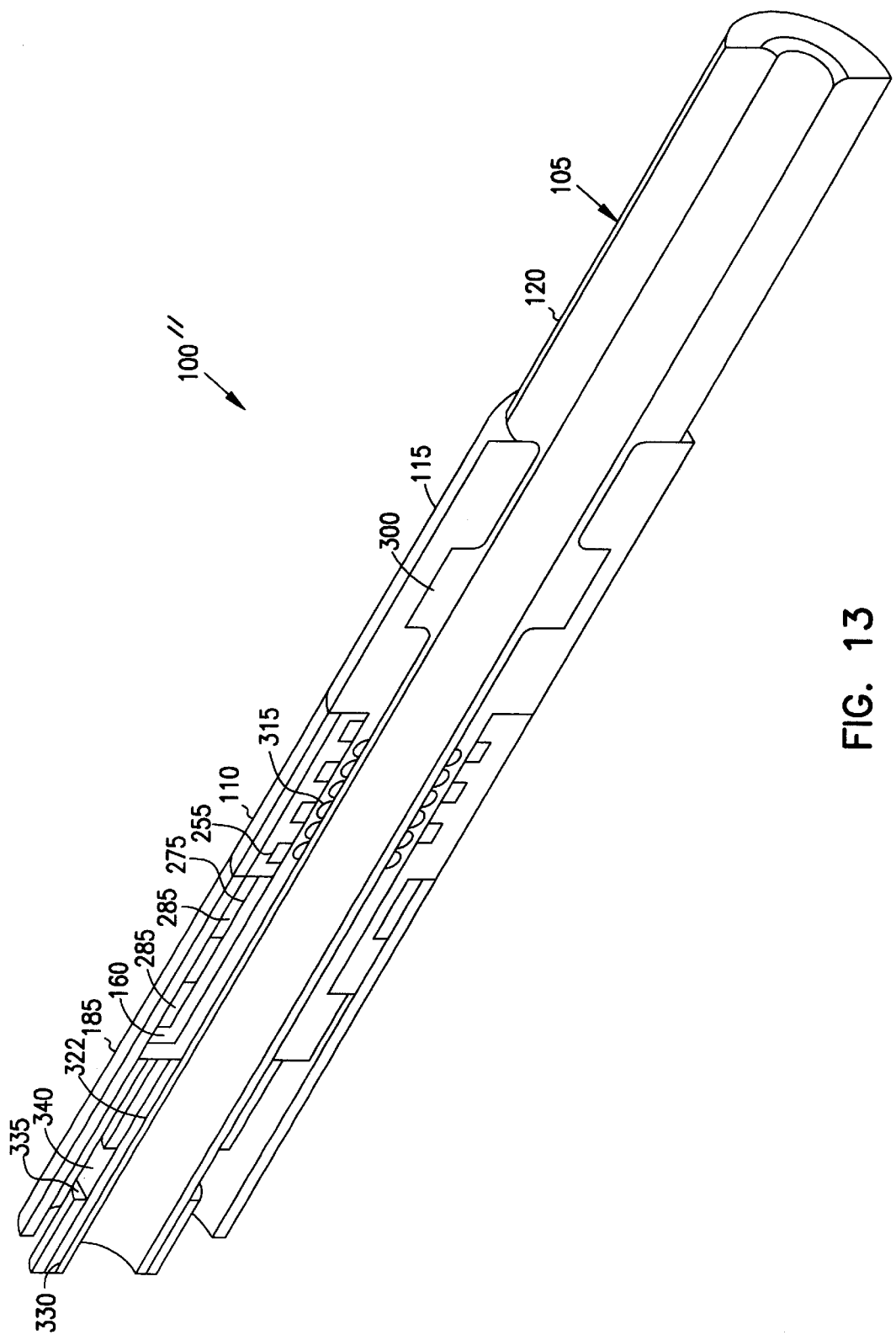
FIG. 13 is a cross-sectional view of a connector assembly as constructed in accordance with one embodiment.

FIG. 13 illustrates an embodiment of a connector assembly 100" including anti-rotation features, for example, pin ridges 310 and/or ring interior grooves 255. These features assist in preventing rotation of the pin 105, ring 110 and unitary sleeve 115 relative to one another.

The connector assembly 100" includes a distal sleeve 330 surrounding the distal portion 322 of the pin 105. The distal sleeve 330 optionally comprises an insulative component that includes an opening 335 exposing a portion of the pin 105 and defining a pin weld zone 340. a conductive element is electrically coupled to the pin 105 in this region, for example, by welding or swaging. The distal sleeve 330 helps to prevent abrasion between a conductive element and the pin 105. Suitable materials and/or configurations for the distal sleeve 330 include, but are not limited to, a separate pre-molded component that is assembled onto the pin, silicone or other biocompatible material. In another option, the distal sleeve 330 is part of the unitary sleeve 115 and is a molded feature of the unitary sleeve 115.

Figure 14:
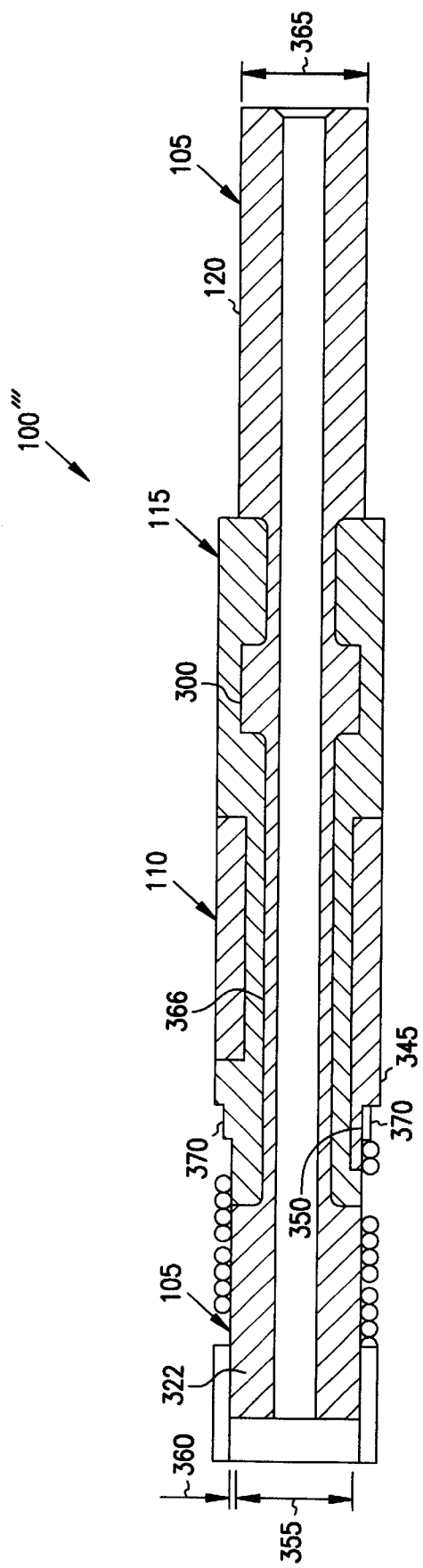
FIG. 14 is a cross-sectional view of a connector assembly as constructed in accordance with one embodiment.
Figure 16A:
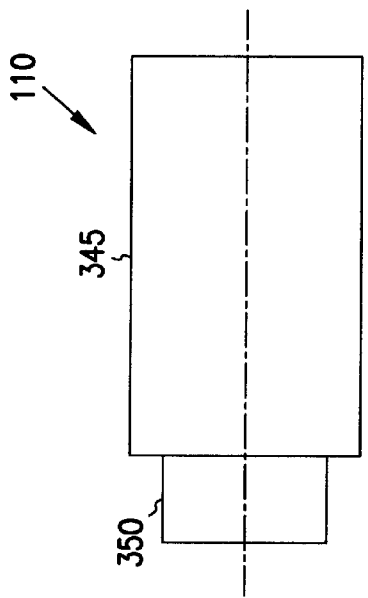
FIG. 16A is a side elevational view of a ring as constructed in accordance with one embodiment.
Figure 16B:
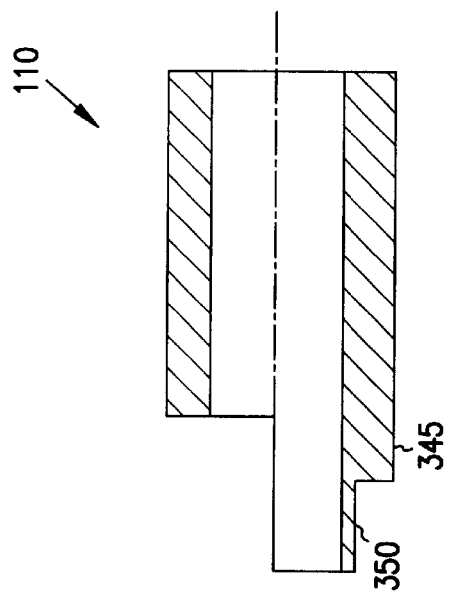
FIG. 16B is a cross-sectional view taken along 16B—16B of FIG. 16D of a ring as constructed in accordance with one embodiment.
Figure 16C:
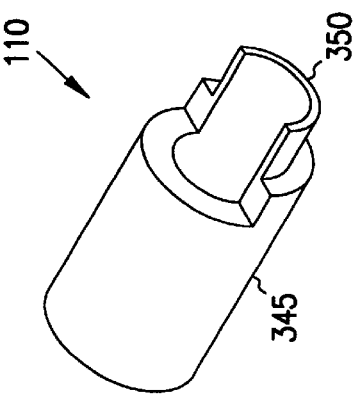
FIG. 16C is a perspective view of a ring as constructed in accordance with one embodiment.
Figure 16D:
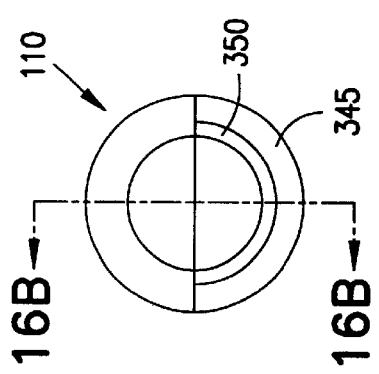
FIG. 16D is an end view of a ring as constructed in accordance with one embodiment.

FIG. 14 illustrates an embodiment of a connector assembly 100''' having a unitary ring 110 with an extension 345 and a step down portion 350 for receiving a connection with at least one conductive element, as shown in FIGS. 16A, 16B, 16C, and 16D. The ring 110 includes an inner ring diameter 355 smaller than the outer distal pin diameter 360 and outer proximal pin diameter 365. The inner ring diameter 355 surrounds an intermediate pin portion 366 having an intermediate diameter and is separated from the intermediate pin portion 366 by the sleeve 115. The ring 110, in one option, is comprised of separate ring halves 116, 118 as shown in FIG. 15. The separate ring halves 116, 118 are assembled in the mold during the molding process to surround the intermediate pin portion 366 of the pin 105. In one embodiment, the separate ring halves 116, 118 are coupled together by welding them together at the interface 117. In another option, the separate ring halves 116, 118 snap together.

As mentioned above, the ring 110 includes an extension 345 with a step down portion 350 for receiving a connection with at least one conductive element. a bonding surface 370 of the sleeve 115 has a reduced diameter to receive a lead body 92 (FIG. 2). As seen in FIGS. 14 and 15, the bonding surface 370 is a continuous surface having a portion that is molded over a portion of the extension 345 step down portion 350, leaving a portion of the step down portion 350 exposed for connection to at least one conductive element. The bonding surface 370 having a reduced diameter allows for the lead body 92 (FIG. 2) to have a diameter that coincides with the exterior portion of the sleeve 115. This provides for a continuous transition, and an isodiameter from the lead body 92 (FIG. 2) to the sleeve 115. In one option, the outer proximal diameter 365 of the pin 105 coincides with the exterior portion of the sleeve 115, the ring 110, and the lead body 92 (FIG. 2). This provides for a continuous profile for the lead body 92 (FIG. 2) and connector assembly 100'''.

Figure 17:
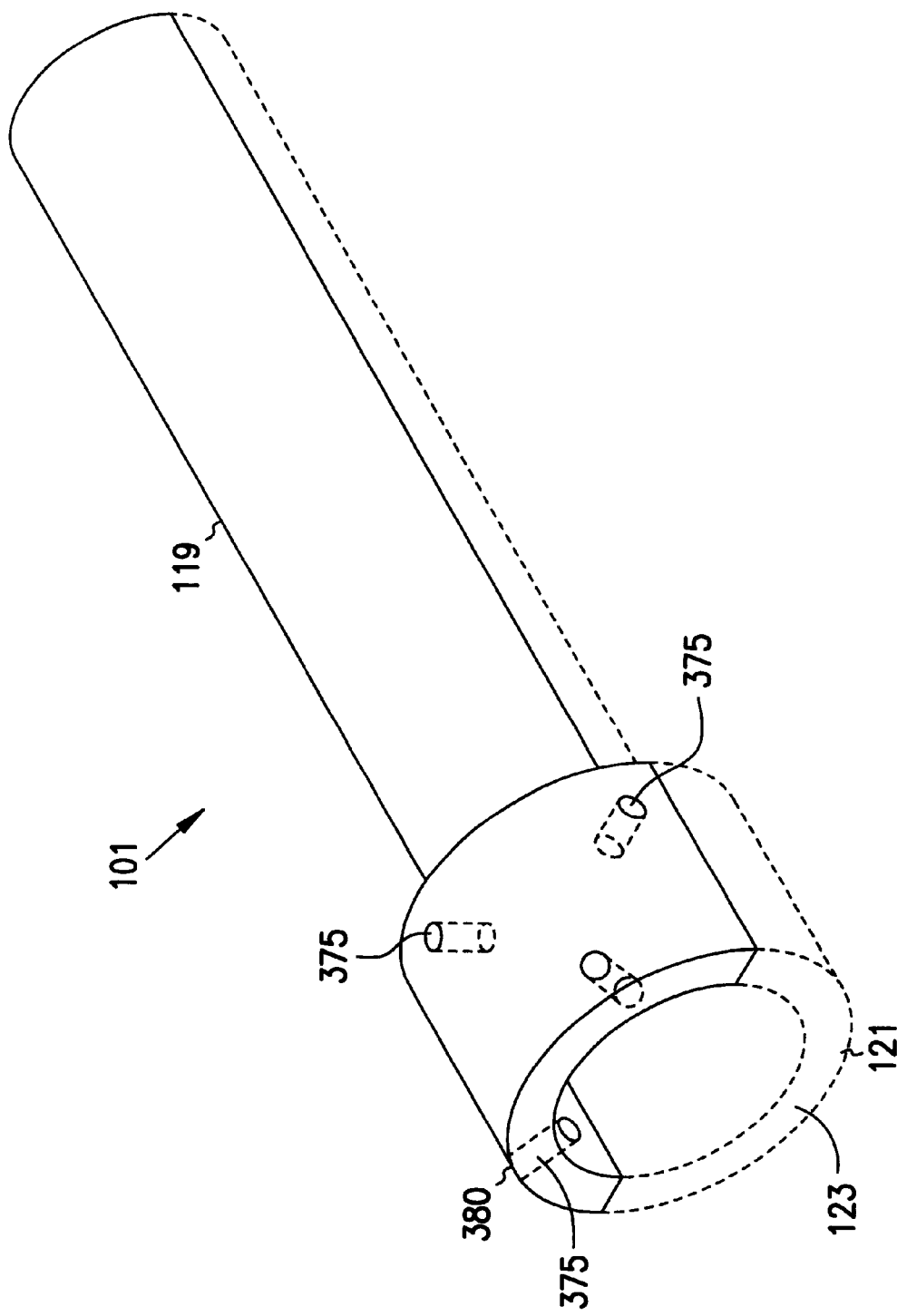
FIG. 17 is a perspective view of a ring as constructed in accordance with one embodiment.

FIG. 17 illustrates another embodiment of the ring 110. The ring includes a first ring half 119. The first ring half 119 includes ring retention features 375, which in one option comprises apertures 380. The apertures 380 receive a portion of the unitary sleeve 115, and assist in retaining the first ring half 119 to the sleeve 115. The second half 121 of the ring 110, in one option, comprises molded material 123.

Figure 18:
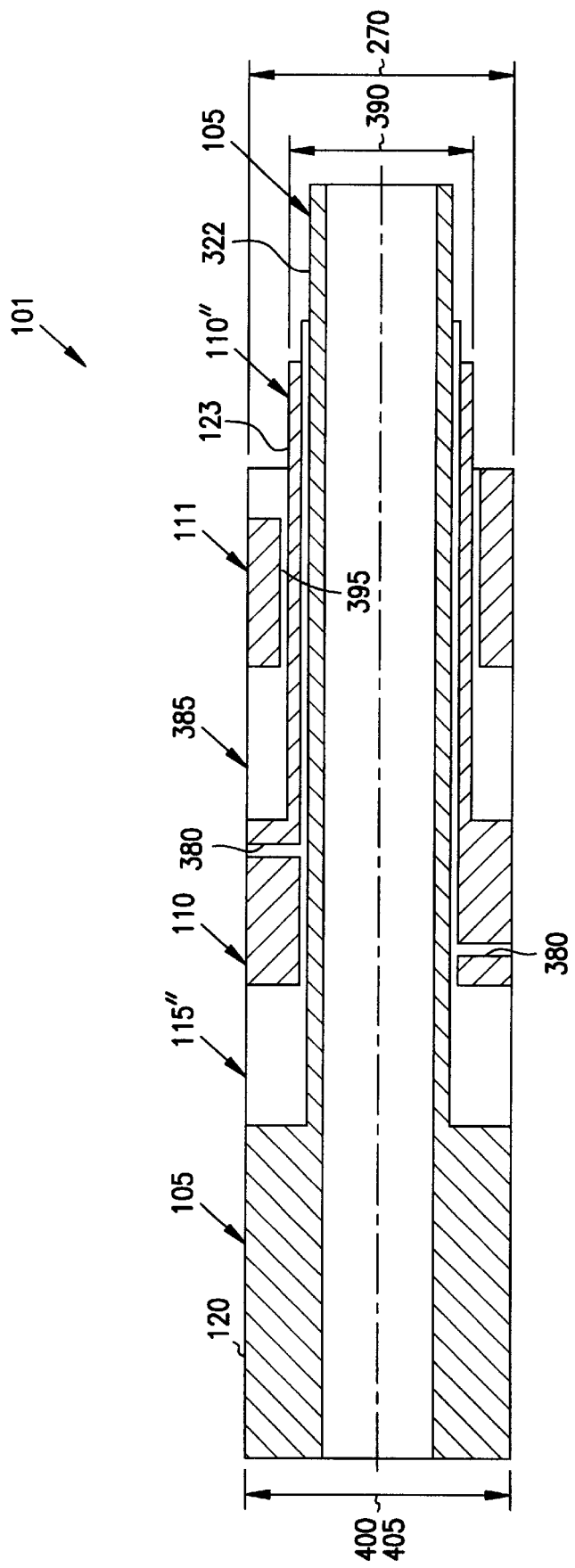
FIG. 18 is a cross-sectional view of a connector assembly as constructed in accordance with another embodiment.

FIG. 18 illustrates an embodiment of a multi-polar connector assembly 101. In one option, the multi-polar connector assembly 101 comprises a tripolar connector assembly. It should be noted that the connector assemblies discussed above are suitable for use with multi-polar assemblies such as tripolar, quadpolar, etc. For example, the multi-polar assembly 101 includes a third unitary ring. Other embodiments include connector assemblies including four rings or greater.

The multi-polar connector assembly 101 includes a pin 105, a first ring 110'', a second ring 111, a first unitary sleeve 115'' comprised of a unitary piece of molded insulative hard polymer, and a second sleeve 385. The first unitary sleeve 115'' mechanically couples the pin 105 and the first ring 110''. The unitary sleeve 115'' also isolates the pin 105 and first ring 110'' such that each is electrically isolated from the other. The second sleeve 385 mechanically couples the first unitary ring 110'' and the second unitary ring 111. The second sleeve 385 also isolates the first ring 110'' and the second unitary ring 111 such that each is electrically isolated from the other.

The first unitary ring 110'' includes a distal ring portion 114 extending distally over the distal pin portion 322. The first ring 110'' includes a distal ring portion 114 that has a distal ring diameter 390 that is reduced from the outer ring diameter 270 to provide for positioning of the second ring 111 over the distal ring portion 114. In one embodiment, the separator sleeve portion 395 between the first ring 10'' and the second ring 111 has a thickness in the range of about 0.005 inches or less.

FIG. 18 illustrates an embodiment in which the second unitary ring 111 includes the features shown in FIG. 4A, FIG. 4B, FIG. 4C, and FIG. 4D for the ring 110. Other embodiments of the second unitary ring 30 include, but are not limited to the features shown and discussed with respect to the ring 110 in FIG. 5, FIG. 6, FIG. 7, FIG. 8, FIGS. 9A–9D, FIG. 10B, FIG. 13, FIG. 14, FIGS. 16A–16D, and FIG. 17.

The outer diameter of the second ring 111 is substantially the same as the diameter 270 of the first ring 110''. The pin 105 has a first diameter 400 at the pin proximal end 120. The sleeve 115'' has an outer diameter 405, where the first pin diameter 400 and the outer sleeve diameter 405 coincide with the outer diameter of the first ring 110'' and the second ring 111. The lead body further coincides with the outer diameter of the connector assembly 101. This forms an isodiametric connector assembly having a continuous uninterrupted profile for the entire connector assembly 101. This simplifies specifications for implantable devices such as pulse generator designs which receive the connector assembly 101.

In one embodiment, the outer diameter of a tripolar connector assembly 101 is in the range of about 0.07–0.12, and in one option 0.07–0.08 inches. In another embodiment, the outer diameter of the tripolar connector assembly 101 is in the range of about 0.08–0.09 inches. The tripolar connector assembly 101 is suitable for use in a pacemaker, cardioverter, anti-tachycardia device, and defibrillator.

In one embodiment, a tripolar connector assembly 101 is manufactured by placing the pin 105, the first ring 110'' and the second ring 111 in a mold, and the first unitary sleeve 115 and second sleeve 385 are molded approximately at the same time around the pin 105, the first ring 110'', and the second ring 111. In one embodiment, the tripolar connector assembly 101 is manufactured with a first ring 110'' having passages in the distal portion of the first ring 110''. During molding, in one option, the insulative hard polymer fills the passages of the first unitary ring 110'' such that first sleeve 115'' and second sleeve 385 are combined as a single unitary sleeve.

a method is further provided, which incorporates the embodiments discussed above, or combinations thereof. The method includes forming a pin, forming at least one ring, molding a sleeve between the pin and the ring, including mechanically coupling the pin with the ring. Several options for the method are as follows. For instance, the method further comprises coupling a lead with the pin, the at least one ring, and the sleeve to form an assembly having an isodiametric outer diameter. In one option, a conductor is coupled with the ring and/or the pin, which can occur before or after the molding process. In addition, a suitable material such as epoxy, or molding material is backfilled over the conductor in another option. In yet another option, the method further includes forming a second ring, and molding the sleeve between the ring, the pin, and the second ring. In yet another option, the method further includes swaging a conductor within a passage of the at least one ring, and/or welding a conductor within a passage of the at least one ring. a further option for the method includes forming an extension on the ring, and/or forming a partial boss and a partial chamfer on the extension.

Various embodiments have been presented for coupling electrically conducting components together, for example, for coupling at least one conductive element to the pin or ring. The welding techniques include, but are not limited to laser welding, resistance welding or butt welding. Other embodiments for coupling a conductor element may include but are not limited to using a conductive adhesive to couple the conductive element to the pin or ring.

In a connector, the size of the components and the area of contact between the components may affect the mechanical strength of the weld or bond and thus may affect the mechanical strength of the connector. One benefit of forming the sleeve from the molded insulative hard polymer is that it allows the connector assembly to be assembled from just the pin, the ring, and the sleeve. Thus, eliminating weld connections between additional components, and eliminating adhesive bonds between components.

Forming the sleeve from the insulative hard polymer also allows the connector assembly to be molded to smaller dimensions while providing an increased pull strength to the connector assembly. Because of the rigidity of the material and because no weld or adhesive bond is required to couple components of the connector assembly, the surface area of the components does not affect the strength of the connection between components. As a result, the connector may include shorter ring lengths while also providing an improved pull strength. In one embodiment, the pull strength is greater than about 10 lbs. In one embodiment, the pull strength is in the range of about 10–25 lbs. In one embodiment, the pull strength is about 25 lbs.

Forming the sleeve from the insulative hard polymer also provides greater dimensional consistency. As a result, the connector assembly has improved tolerances. Thus, the connector assembly provides the necessary fit with the structure of the pulse generator with an improved assembly process. The dimensional consistency and mechanical strength is maintained in the radial direction by the rigidity of the material.

Advantageously, the connector assembly has fewer components, fewer steps in the assembly process, improved size, improved insulative properties and improved mechanical strength than previous connector assemblies. Since the connector is made with a smaller volume, the device with which the connector operates can be made smaller, for example the header. Furthermore, the connector design allows for greater dimensional consistency. Possible applications of the connector assembly include, but are not limited to, cardiac stimulators such as a pacemaker, an anti-tachycardia device, a cardioverter, or a defibrillator. Although pulse generators for cardiac stimulators have been discussed, application of the connector assembly is not to be limited to use with a cardiac stimulator. For instance, the connector assembly is suitable for use with neural transmitter lead assemblies and other applications as well. In addition, the connector assembly is suitable for use with other sources of electrical energy, sensing instruments or combinations of devices. It should be further noted that the connector assembly is suitable for use in low and high voltage applications in a single port.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A connector assembly comprising:
    a pin extending from a pin distal end to a pin proximal end, and having a pin intermediate portion therebetween;
    at least one ring extending from a ring distal end to a ring proximal end and having a ring intermediate portion therebetween;
    a molded insulative polymer between the pin and the ring, the polymer mechanically coupling the pin and the ring, and the insulative polymer insulating the pin from the ring;
    wherein the pin includes at least one chamfer formed thereon.

2. The connector assembly as recited in claim 1, wherein the pin has a first outer diameter and the ring has a second outer diameter, and the first diameter is substantially the same as the second diameter.

3. The connector assembly as recited in claim 1, further comprising a second ring, and the insulative polymer is between the pin, the first ring and the second ring, the second ring mechanically coupled to the pin by the polymer.

4. The connector assembly as recited in claim 1, wherein the ring further includes at least one passage, and the molded polymer is molded within the at least one passage.

5. The connector assembly as recited in claim 1, wherein the molded insulative polymer is molded within the chamfer.

6. The connector assembly as recited in claim 1, wherein the ring includes a full boss and a full chamfer.

7. The connector assembly as recited in claim 1, wherein an interior surface of the ring includes grooves formed thereon.

8. The connector assembly as recited in claim 7, wherein the grooves are oblique to a longitudinal axis of the ring.

9. The connector assembly as recited in claim 1, wherein the pin further includes a boss formed thereon.

10. The connector assembly as recited in claim 9, wherein the pin boss further includes grooves formed thereon.

11. The connector assembly as recited in claim 10, wherein the pin further includes grooves formed on a distal portion of the pin.

12. The connector assembly as recited in claim 1, wherein the connector assembly further includes a groove on an outer diameter of the connector assembly, the groove configured to receive a portion of a pulse generator.

13. A connector assembly comprising:
    a pin extending from a pin distal end to a pin proximal end, and having a pin intermediate portion therebetween;
    at least one ring extending from a ring distal end to a ring proximal end and having a ring intermediate portion therebetween;
    a molded insulative polymer between the pin and the ring, the polymer mechanically coupling the pin and the ring, and the insulative polymer insulating the pin from the ring;
    the ring includes a full boss and a full chamfer;
    wherein the ring includes an extension thereon, the extension having a partial boss and a partial chamfer thereon.

14. An assembly comprising:
a connector assembly including:
- a pin extending from a pin distal end to a pin proximal end, and having a pin intermediate portion therebetween;
- at least one ring extending from a ring distal end to a ring proximal end and having a ring intermediate portion therebetween;
- a molded insulative polymer between the pin and the ring, the polymer mechanically coupling the pin and the ring, and the insulative polymer insulating the pin from the ring; and a lead having a lead body, the lead coupled with the connector assembly
wherein the connector assembly further includes a groove on an outer diameter of the connector assembly, the groove configured to receive a portion of a pulse generator.

15. The connector assembly as recited in claim 14, wherein the pin has at least one chamfer formed thereon.

16. The connector assembly as recited in claim 14, wherein the connector assembly has a first outer diameter, the lead having a second outer diameter, and the first outer diameter and the second outer diameter are substantially the same.

17. The connector assembly as recited in claim 14, wherein the connector assembly further includes a second groove on the outer diameter.

18. The connector assembly as recited in claim 14, further comprising a second ring, and a third ring, and the insulative polymer is between the pin, the first ring, the second ring, and the third ring, the second ring and the third ring mechanically coupled to the pin by the polymer.

19. The connector assembly as recited in claim 14, wherein the pin further includes a pin boss formed thereon, and the pin boss further includes grooves formed thereon.

20. A method comprising:
forming a pin;
forming at least one ring; and
molding a sleeve between the pin and the ring, including mechanically coupling the pin with the ring;
coupling a conductor with the ring and/or the pin prior to molding the sleeve.

21. The method as recited in claim 20, further comprising coupling a lead with the pin, the at least one ring, and the sleeve to form an assembly having an isodiametric outer diameter.

22. The method as recited in claim 20, further comprising forming a second ring, and molding the sleeve between the ring, the pin, and the second ring.

23. The method as recited in claim 20, further comprising swaging a conductor within a passage of the at least one ring.

24. The method as recited in claim 20, further comprising welding a conductor within a passage of the at least one ring.

25. The method as recited in claim 20, further comprising forming an extension on the ring.

26. The method as recited in claim 25, further comprising forming a partial boss and a partial chamfer on the extension.

27. The method as recited in claim 26, further comprising forming a full boss and a full chamfer on the at least one ring.

28. The method as recited in claim 20, further comprising forming ridges in the pin, and molding polymer material within the ridges.

29. The method as recited in claim 20, further comprising forming ridges in the pin at an angle oblique to a longitudinal axis of the pin, and molding polymer material within the ridges.

30. The method as recited in claim 20, wherein mechanically coupling the pin with the ring includes forming an isodiametric connector assembly.

31. A method comprising:
forming a pin;
forming a chamfer on the pin;
mechanically coupling the pin with the ring; and
insulating the pin from the ring including molding a sleeve between the pin and the ring.

32. The method as recited in claim 31, further comprising coupling a conductor with the ring and/or the pin.

33. The method as recited in claim 31, wherein coupling the conductor occurs prior to molding the sleeve.

34. The method as recited in claim 31, further comprising forming ridges in the pin at an angle oblique to a longitudinal axis of the pin, and molding polymer material within the ridges.

* * * * *

UNITED STATES PATENT AND TRADEMARK OFFICE
CERTIFICATE OF CORRECTION

PATENT NO.     : 6,643,550 B2
DATED          : November 4, 2003
INVENTOR(S)    : Gwen Crevensten et al.

It is certified that error appears in the above-identified patent and that said Letters Patent is hereby corrected as shown below:

<u>Column 14,</u>
Line 37, delete "claim 31" and insert -- claim 32 -- therefor.

Signed and Sealed this

Ninth Day of March, 2004

JON W. DUDAS
*Acting Director of the United States Patent and Trademark Office*